United States Patent [19]
Baranowski, Jr. et al.

[11] Patent Number: 5,458,627
[45] Date of Patent: Oct. 17, 1995

[54] ELECTROCHEMICALLY CONTROLLED FARADIC STIMULATION OF OSTEOGENESIS

[75] Inventors: Thomas J. Baranowski, Jr., Snellville, Ga.; Jonathan Black, King of Prussia, Pa.

[73] Assignee: Electro-Biology, Inc., Parsippany, N.J.

[21] Appl. No.: 92,274

[22] Filed: Jul. 15, 1993

Related U.S. Application Data

[63] Continuation-in-part of Ser. No. 47,743, Apr. 15, 1993, abandoned, which is a continuation of Ser. No. 962,507, Oct. 15, 1992, abandoned.

[51] Int. Cl.$^6$ ................................................. A61N 1/18
[52] U.S. Cl. ................................................. 607/51; 607/52
[58] Field of Search .................................. 607/50, 51, 52

[56] References Cited

U.S. PATENT DOCUMENTS

| | | |
|---|---|---|
| 3,842,841 | 10/1974 | Brighton et al. . |
| 3,848,608 | 11/1974 | Leonard . |
| 4,026,304 | 5/1977 | Levy . |
| 4,333,469 | 6/1982 | Jeffcoat et al. . |
| 4,430,999 | 2/1984 | Brighton et al. . |
| 4,442,846 | 4/1984 | Brighton et al. . |
| 4,506,674 | 3/1985 | Brighton et al. . |
| 4,509,520 | 4/1985 | Dugot . |
| 4,519,394 | 5/1985 | Black et al. . |
| 4,620,543 | 11/1986 | Heppenstall et al. . |
| 4,889,111 | 12/1989 | Ben-Dov et al. . |
| 5,056,518 | 10/1991 | Pethica et al. . |

OTHER PUBLICATIONS

Brighton, Carl T. et al., "Electrical Stimulation and Oxygen Tension," *Annals N.Y. Acad. Sci.* 238:314–320 (1974).
Brighton, Carl T. et al., "Cathodic Oxygen Consumption and Electrically Induced Osteogenesis," *Clin. Orthop. Rel. Res.* 107:277–282 (1975).
Spadaro, Joseph A., "Bioelectrochemical studies of Implantable Bone Stimulation Electrodes," *Bioelectrochem. Bioenergetics* 5:232–238 (1978).
Spadaro, Joseph A., "Electrical Osteogenesis—Role of the Electrode Material," In: Electrical Properties of Bone and Cartilage. Experimental Effects and Clinical Applications, Brighton, Black and Pollack, eds., Grune and Stratton, New York, 189–196 (1979).
Black, Jonathan et al., "Mechanisms of Stimulation of Osteogenesis by Direct Current," In: Electrical Properties of Bone and Cartilage. Experimental Effects and Clinical Applicaton. Brighton, Black and Pollack, eds., Grune and Stratton, New York, 215–224 (1979).
Brighton, C. T., "Present and Future of Electrically Induced Osteogenesis," *In: Clinical Trends In Orthopaedics* Ed: Straub and Wilson, Jr., Thieme–Stratton, N.Y., 1–15 (1982).

(List continued on next page.)

*Primary Examiner*—William E. Kamm
*Assistant Examiner*—Scott M. Getzow
*Attorney, Agent, or Firm*—Woodard, Emhardt, Naughton, Moriarty & McNett

[57] ABSTRACT

Invented are methods and an apparatus for faradic stimulation of osteogenesis by control of electrochemical reactions through maintenance of a stimulus between a cathode and anode yielding only beneficial electrochemical reactions at the cathode, the site of desired osteogenesis, while preventing any detrimental reaction at the same. Said methods and apparatus maintain a stimulus yielding the maximum acceptable level of oxygen consumption and pH elevation at the cathode, either with or without the formation of hydrogen peroxide as only an intermediate chemical species, while preventing the initiation of hydrogen gas evolution at the same such that the stimulus results in depression of oxygen tension plus elevation of pH, environmental effects that favor osteogenesis, and prevents a reaction resulting in elevation of pH plus hydrogen gas evolution, the latter effect being detrimental to the same.

32 Claims, 9 Drawing Sheets

OTHER PUBLICATIONS

Baranowski, Thomas J. et al., "Microenvironmental Changes Associated With Electrical Stimulation of Osteogenesis by Direct Current," *Trans. Bioelectrical Repair Growth Soc.* 2:47 (1982).

Baranowski, Thomas J. et al., "Microenvironmental Changes and Electrodic Potentials Associated With Electrical Stimulation of Osteogenesis by Direct Current," *Trans. Orthop. Res. Soc.* 8:258 2:47 (1983).

Baranowski, Thomas J. et al., "The Role of Cathodic Potential in Electrical Stimulation of Osteogenesis by Direct Current" *Trans. Orthop. Res. Soc.* 8:352 (1983).

Baranowski, Thomas J. et al., "The Role of Cathodic Potential in Electrical Stimulation of Osteogenesis by Direct Current," *Trans. Bioelectrical Repair Growth Soc.* 3:34 (1983).

Baranowski, Thomas J., Jr., "Electrical Stimulation of Osteogenesis by Direct Current: Electrochemically–Mediated Microenvironmental Alterations," Ph. D. Thesis, University of Pennsylvania, Philadelphia, Pennsylvania, title page, pp. 62–72, 87–90, 211, 213–217, 233, 244–245 (1983).

Dymecki, S. M. et al., "The Cathodic Potential Dose–response Relationship for Medullary Osteogenesis with Stainless Steel Electrodes," *Trans. Bioelectrical Repair Growth Soc.* 4:29 (1984).

Black, Jonathan et al., "Electrochemical Aspects of d.c. Stimulation of Osteogenesis," *Bioelectrochem. Bioenergetics* 12:323–327 (1984).

Baranowski, Thomas J. et al., "The Mechanism of Faradic Stimulation of Osteogenesis," In: Mechanistic Approaches to Interactions of Electric and Electromagnetic Fields with Living Systems, M. Blank and E. Findl, eds., Plenum Publishing Corp., New York, 399–416 (1987).

| | |
|---|---|
| A $H_2O_2 + 2H^+ + 2e^- \leftrightarrow 2H_2O$ | F $O_2 + 2H^+ + 2e^- \leftrightarrow H_2O_2$ |
| B $H_2O_2 + 2e^- \leftrightarrow 2OH^-$ | G $O_2 + 2H_2O + 2e^- \leftrightarrow H_2O_2 + 2OH^-$ |
| C $HO_2^- + 2e^- + H_2O \leftrightarrow 3OH^-$ | H $O_2 + H_2O + 2e^- \leftrightarrow HO_2^- + OH^-$ |
| D $O_2 + 4H^+ + 4e^- \leftrightarrow 2H_2O$ | I $2H^+ + 2e^- \leftrightarrow H_2$ |
| E $O_2 + 2H_2O + 4e^- \leftrightarrow 4OH^-$ | J $2H_2O + 2e^- \leftrightarrow H_2 + 2OH^-$ | though electrical stimulation of osteogenesis relates generally to electrical stimulation of osteogenesis and specifically to a new method and apparatus for implementing faradic stimulation where electricity is delivered through electrodes.

ELECTROCHEMICALLY CONTROLLED FARADIC STIMULATION OF OSTEOGENESIS

CROSS-REFERENCE TO RELATED APPLICATIONS

This application is a continuation-in-part of U.S. patent application Ser. No. 08/047,743, filed Apr. 15, 1993, now abandoned which is a continuation of U.S. patent application Ser. No. 07/962,507, filed Oct. 15, 1992 now abandoned.

BACKGROUND OF THE INVENTION

This invention relates generally to electrical stimulation of osteogenesis and specifically to a new method and apparatus for implementing faradic stimulation where electricity is delivered through electrodes.

Electricity is known to stimulate osteogenesis for the treatment of bone disorders although the mechanism by which such stimulation occurs is not precisely known. Three different techniques of electrical stimulation are presently available: faradic, inductive, and capacitive. Of these techniques, faradic stimulation is the oldest historically, the most basic physically, and the most theoretically understood in terms of mechanism. Faradic stimulation involves a net transfer of charge through biological tissue between, typically, an implanted cathode, the negative electrode where osteogenesis occurs, and either an implanted or a topical anode, the positive electrode required only to complete the electrical circuit. A primary electric field, but no magnetic field, is produced at each electrode. Although these exogenous electric fields can alter the endogenous electric fields locally in tissue, the predominant theory offered to explain faradic effects is based on electrochemical reactions that occur at the electrodes. Through these reactions, the products created and the reactants consumed may individually or jointly cause a cellular response. In terms of the actual faradic signal, a constant direct current between cathode and anode is used clinically at present although a constant cathodic potential, the potential between cathode and a reference electrode, is regarded as an improved signal and may find future clinical use.

Prior art systems with a constant direct current signal, described, for example, in U.S. Pat. No. 3,842,841 issued to Brighton et al. on Oct. 22, 1994 and in an article entitled "Present and Future of Electrically Induced Osteogenesis" in Clinical Trends in Orthopaedics, edited by L. R. Straub and P. D. Wilson, Jr., published by Thieme-Stratton, New York, N.Y. 1982, pages 1–15, are designed to maintain a constant current regardless of changes in resistance between cathode and anode. To maintain a constant direct current, the interelectrode potential between cathode and anode as well as the electrodic potentials of the cathode and anode, each with respect to a reference electrode, are permitted to vary. The latter potentials are known generally as electrodic potentials or specifically as cathodic and anodic potentials. Electrochemically, current dictates the rate at which a reaction occurs at an electrode while the electrodic potential dictates the type of reaction and facilitates the relative ease by which that reaction occurs. A constant direct current will, therefore, dictate a constant reaction rate, but the type of reaction and the relative ease by which it occurs can change because the electrodic potential is permitted to vary. Thus, a constant direct current signal believed to be optimal initially may, over the course of chronic use, fall below optimal and become less stimulatory or rise above optimal and become detrimental due, in both cases, to changes in electrodic potential and, subsequently, changes in the type of reaction.

Prior art systems with a constant cathodic potential signal, described, for example, in U.S. Pat. No. 4,519,394 issued to Black et al. on May 28, 1985, which is hereby incorporated by reference, are designed to maintain a constant potential between the cathode and a reference electrode regardless of changes in resistance between cathode and anode. To maintain a constant cathodic potential, the current, the interelectrode potential between cathode and anode, and the anodic potential with respect to the reference electrode are permitted to vary. Electrochemically, as described above, a constant cathodic potential will dictate the type of reaction and the relative ease by which that reaction occurs, but the reaction rate can change because the current is permitted to vary. Thus, a constant cathodic potential signal believed to be optimal initially may, over the course of chronic use, fall below optimal and become less stimulatory due to decreases in current and, subsequently, decreases in the reaction rate. Note, however, that, unlike a constant direct current signal, a constant cathodic potential signal cannot rise above optimal and become detrimental since the cathodic potential is controlled to prevent a change in reaction type. For this reason alone, a constant cathodic potential signal is regarded as an improvement over a constant direct current signal.

Electrochemical reactions, involving electrons which act at the interface between a metal or metallic conduction phase and an electrolyte, occur at electrodes employed in faradic stimulation. As first reported in the article entitled "Electrical Stimulation and Oxygen Tension" by Brighton et al. in Annals of the New York Academy of Sciences, 238, 1974, pages 314–320, hereinafter Brighton et al. (1974), and, in more technical detail, in the article entitled "Cathodic Oxygen Consumption and Electrically Induced Osteogenesis" by Brighton et al. in Clinical Orthopaedics and Related Research, 107, 1975, pages 277–282, hereinafter Brighton et al. (1975), evidence of electrochemical reactions at typical faradic electrodes has been obtained in vitro where consumption of oxygen, elevation of pH, and evolution of hydrogen have all been found to occur at the cathode depending upon the magnitude of the constant direct current. Evidence of electrochemical reactions can also be found from polarization or potentiostatic studies performed with the electrodes either in vitro or in vivo. In a polarization study, a set potential is applied to the cathode (negative) and anode (positive), and then measurements are made of the resultant (a) direct current between cathode and anode, (b) the cathodic potential which is the potential of the cathode with respect to a reference electrode, and (c) the anodic potential which is the potential of the anode with respect to the same reference electrode. In a potentiostatic study, a potential is again applied to the cathode and anode but is permitted to vary in order to result in, by choice, either a set cathodic or anodic potential, and then measurements are made of the resultant (a) direct current between cathode and anode, (b) the interelectrode potential which is the potential applied to the cathode and anode, and (c) either the anodic potential, if a set cathodic potential was chosen, or the cathodic potential, if a set anodic potential was chosen. In either study, the set potential is adjusted over a range from usually zero (0) to less than five (5) volts over time in order to produce a plot of the cathodic and anodic potentials, both with respect to a reference electrode, versus the resulting direct current between cathode and anode, usually with the direct current on logarithmic (log) scale.

An example of a plot from polarization studies performed in vivo with a cathode and anode, both of stainless-steel, in rabbits at implantation sites appropriate for faradic stimulation is presented in FIG. 1, which is extracted from pages 406–407 of "The Mechanism of Faradic Stimulation of Osteogenesis" by Baranowski et al. in Mechanistic Approaches to Interactions of Electric and Electromagnetic Fields With Living Systems, edited by M. Blank and E. Findl, published by Plenum Publishing Corporation, New York, N.Y. 1987, pages 399–416, hereinafter Baranowski et al. (1987), which article is hereby incorporated by reference. Two curves, the result of polynomial regression analyses, are shown for the cathodic and anodic potentials, both with respect to a silver/silver chloride (Ag/AgCl) reference electrode, versus the direct current on log scale. The curves exemplify the relationship between the electrodic potentials and the direct current, essentially the electrochemical behavior of the electrodes, for the specific set of conditions under which the polarization studies were performed.

Of particular interest here is the electrochemical behavior of the cathode since the cathode is the site of osteogenesis in faradic stimulation whereas the anode only serves to complete the circuit. For the cathode, three regions of relatively uniform slope can be distinguished from the curve of cathodic potential versus the direct current shown in FIG. 1. Consecutive regions of uniform slope are joined by a change in slope which takes place at two different locations. The cathodic potential at each of these two slope changes can be determined graphically by superimposing a straight line on each of the three regions of uniform slope until the lines from consecutive regions intersect. When this was performed on the cathodic curve in FIG. 1, the cathodic potentials at the slope changes were found to be −0.59 and −1.26 volt with respect to an Ag/AgCl reference electrode.

In order to identify which reactions occur at an in vivo cathode, the above potentials can be compared to equilibrium potentials of reactions possible in vivo from a potential versus pH diagram. Such a diagram has been developed, as shown in FIG. 2 which is extracted from pages 403–406 of the above-referenced article by Baranowski et al. (1987), from expressions for equilibrium potentials of electrochemical reactions provided in a book by Pourbaix entitled *Atlas of Electrochemical Equilibria in Aqueous Solutions*, published by Pergamon Press, Oxford, United Kingdom, 1966, hereinafter Pourbaix 1966), for conditions typically found initially at the cathode in vivo and for potentials with respect to an Ag/AgCl reference electrode. Because water, oxygen, hydrogen ions, and hydroxyl ions constitute the predominant chemical species available as reactants in vivo, only reactions involving these reactants as well as hydrogen, hydrogen peroxide, and hydrogen peroxide ion as products from these reactants are considered possible. The dashed vertical line shown in FIG. 2 at an in vivo pH of 7.4 intersects each of the four solid, sloped lines, representing possible reactions, at the potential indicated. A point can be chosen along the vertical line for any particular electrode potential. If the necessary reactants are available, reactions below this chosen point will occur as oxidations at anodes while reactions above the chosen point will occur as reductions at cathodes.

The −0.59 volt potential of the first slope change found in FIG. 1 is comparable to the −0.5211 volt equilibrium potential of the reaction $O_2+2H_2O+2e^- \leftrightharpoons H_2O_2+2OH^-$ given in FIG. 2 whereas the −1.26 volt potential of the second slope change found in FIG. 1 is comparable to the −1.2031 volt equilibrium potential of the reaction $2H_2O +2e^- \leftrightharpoons H_2+ 2OH^-$ given in FIG. 2. From this comparison of potentials, a most probable reduction reaction can be related to each of the three regions of uniform slope described for the curve of cathodic potential versus the direct current on log scale.

FIG. 3, which is extracted from pages 407–408 of the above-referenced article by Baranowski et al. (1987), is a generic curve of the cathodic potential versus the direct current on log scale with a reduction process indicated for each of its three regions of relatively uniform slope. This curve depicts the idealized relationships between the cathodic potential and the direct current for a cathode in general and, for this reason, has been drawn with unnumbered axes. However, equilibrium potentials for the reactions determined theoretically from the potential versus pH diagram in FIG. 2 are given in comparison to the potentials of the two slope changes determined experimentally from the in vivo polarization studies presented in FIG. 1.

Referring to FIG. 3, the reduction reaction $O_2+2H_2O +4e^- \rightarrow 4OH^-$ occurs in the first region. This oxygen consumption and pH elevation reaction occurs through a single, 4-electron reaction. Two reduction reactions, $O_2+2H_2O+2e^- \rightarrow H_2O_2+2OH^-$ plus $H_2O_2+2e^- \rightarrow 2OH^-$, occur in the second region, due to the reduction upon production of hydrogen peroxide, to give the overall reaction $O_2+2H_2O+4e^- \rightarrow 4OH^-$. This process of intermediate hydrogen peroxide formation, oxygen consumption, and pH elevation occurs through two, 2-electron reactions. The initiation of these two, 2-electron reactions displaces the previous, single, 4-electron reaction which accounts for the first change in slope observed from the curve of the cathodic potential versus the direct current. Finally, the reduction reaction $2H_2O+2e^- \rightarrow H_2+2OH^-$ occurs in the third region. This hydrogen evolution and pH elevation reaction occurs through a single, 2-electron reaction. The initiation of this single, 2-electron reaction displaces the two, 2-electron reactions which then accounts for the second change in slope.

Under conditions typically found initially in vivo and with respect to an Ag/AgCl reference electrode, the following observations can be made from the analysis of the curve of the cathodic potential versus the direct current and from the comparison of the cathodic potentials at slope changes to the equilibrium potentials of reactions from the potential versus pH diagram. First, a reduction reaction involving oxygen consumption and pH elevation is predicted to occur at a cathode when the cathodic potential is between +0.025 and −0.5211 volt. Second, the same overall reaction is also predicted to occur when the cathodic potential is between −0.5212 and −1.2031 but with the intermediate formation of hydrogen peroxide. Finally, when the cathodic potential is greater than −1.2031 volt, a reduction reaction involving hydrogen evolution and pH elevation is then predicted to occur. Thus, a depressed oxygen tension, an elevated pH, and hydrogen gas formation should be found at an in vivo cathode depending on its potential.

As initially reported in an abstract entitled "Microenvironmental Changes Associated with Electrical Stimulation of Osteogenesis by Direct Current" by Baranowski et al. in *Transactions of the Bioelectrical Repair and Growth Society*, 2nd Annual Meeting, 1982, page 47 and, in a more detailed publication, in a doctoral dissertation entitled *Electrical Stimulation of Osteogenesis by Direct Current: Electrochemically-Mediated Microenvironmental Alterations* by Baranowski for the University of Pennsylvania, Philadelphia, Pa., 1983, hereinafter Baranowski (1983), the oxygen tension and pH near a cathode during in vivo faradic stimulation of osteogenesis by constant direct currents were determined and then correlated to the resultant biological response. Depression of oxygen tension and elevation of pH were found to occur at the cathode as a result of reduction processes that are influenced by the cathodic potential of the stimulus. The overall observations strongly indicated that alterations in oxygen tension and pH mediated by the reduction processes at the cathode are actually related to, rather than merely associated with, the biological response elicited by the stimulus. This view is supported by observations that osteogenesis occurs under low oxygen tension and high pH in the absence of electrical stimulation. In fact, many studies have examined the relationship between bone growth and either oxygen tension or pH. The conclusions from these studies are, first, that bone cells follow a predominantly anaerobic metabolic pathway; second, that low oxygen tension and high pH exist at sites of calcification and bone formation; and, third, that high oxygen tension and low pH favors bone resorption rather than formation. Together, the evidence from other studies reinforces the hypothesis that the biological response to faradic stimulation is actually a response to the microenvironmental alterations of oxygen tension and pH mediated by reduction processes at the cathode. This view is in general agreement with early proposed mechanisms of faradic stimulation as presented in the above-referenced articles by Brighton et al. (1974, 1975); in the article entitled "Mechanisms of Stimulation of Osteogenesis by Direct Current" by Black et al. in *Electrical Properties of Bone and Cartilage. Experimental Effects and Clinical Applications*, edited by C. T. Brighton, J. Black, and S. R. Pollack, published by Grune and Stratton, New York, N.Y. 1979, pages 215–224, hereinafter Black et al. (1979), which is hereby incorporated by reference; and, in more detail, in the above-referenced doctoral dissertation by Baranowski (1983) and in the article entitled "Electrochemical Aspects of D.C. Stimulation of Osteogenesis" by Black et al. in *Bioelectrochemistry and Bioenergetics*, 12, 1984, pages 323–327.

On the supposition that electrochemically mediated, microenvironmental alterations of oxygen tension and pH elicit the biological response to faradic stimuli, a number of overall conclusions can be made with regard to faradic stimulation.

First, although an anode, or a predominantly positive electrode, is required to complete the circuit in faradic stimulation, it will not be the site of non-traumatic osteogenesis. The potential versus pH diagram shown in FIG. 2 can be employed to predict that oxidation reactions involving oxygen evolution, rather than oxygen consumption, and pH depression, rather than pH elevation, occur at an in vivo anode depending on its potential. Other potential versus pH diagrams, not shown here, would predict that oxidation reactions involving production of chlorine or metallic ions could also occur at this electrode. In addition, intermediate free radicals of oxygen and chlorine may be produced during oxidation reactions involving the evolution of oxygen and chlorine. However, although microenvironmental alterations can be produced at the anode, an elevated oxygen tension and a low pH are conditions appropriate for bone resorption, rather than bone formation, while the presence of chlorine, metallic ions, and free radicals are judged to be cytotoxic if present in sufficient local concentrations. To prevent such reactions and resulting alterations from occurring in vivo during faradic stimulation of osteogenesis, a typical anode is much larger than a cathode in surface area which permits passage of a large current at a very small anodic potential.

Second, although current dictates the rate at which a reduction process occurs at the cathode, the cathodic potential dictates the type of reduction process and facilitates the relative ease by which that reaction occurs. As reported in an abstract entitled "The Role of Cathodic Potential in Electrical Stimulation of Osteogenesis by Direct Current" by Baranowski et al. in *Transactions of the Orthopaedic Research Society*, 8th Annual Meeting, 1983, page 352, the role of the cathodic potential in faradic stimulation of osteogenesis has been examined by employing cathodes of different metal exposures with a 20 microampere stimulus to obtain cathodes at different potentials but at a fixed, constant direct current. They found that the magnitude of an osteogenic response, free from evidence of necrosis or void spaces which are indicative of hydrogen gas evolution at the cathode, increased directly with cathodic potential over a range from −0.6 to −1.23 volt with respect to Ag/AgCl. From −1.26 to −1.4 volt with respect to Ag/AgCl, the magnitude of the osteogenic response decreased and areas of necrosis and void spaces increased directly with cathodic potential. Based on this and related observations, selection of an appropriate direct current is necessary but not sufficient for faradic stimulation of osteogenesis since, on a proportional basis, differences in cathodic potential produce greater differences in osteogenesis than equivalent differences in current. This has been verified by the finding that equal or greater magnitudes of osteogenesis were elicited by controlled, cathodic potential stimuli between −1.15 and −1.25 volt with respect to Ag/AgCl when compared to a constant direct current of 20 microamperes using identical electrodes, as reported in a abstract entitled "The Cathodic Potential Dose-Response Relationship for Medullary Osteogenesis with Stainless Steel Electrodes" by Dymecki et al. in *Transactions of the Bioelectrical Repair and Growth Society*, 4th Annual Meeting, 1984, page 29.

Third, since osteogenesis is dependent on the degree of microenvironmental alteration which is then dependent on the rate at which a reduction process occurs at the cathode, the more current delivered at an optimum cathodic potential, the greater the degree of microenvironmental alteration, and, if such alteration is tolerable, the greater the magnitude of osteogenesis.

Lastly, although the generic curve of the cathodic potential versus the direct current on log scale, shown in FIG. 3, was, in part, developed from polarization studies performed with specific, stainless-steel electrodes under conditions typically found initially in vivo and with an Ag/AgCl reference electrode, the three regions of relatively uniform slope and the two slope changes can be identified from polarization or potentiostatic studies performed with electrodes of any design or composition as well as any reference electrode. This is evident in reports entitled "Bioelectrochemical Studies of Implantable Bone Stimulation Electrodes" by Spadaro in *Bioelectrochemistry and Bioenergetics*, 5, 1978, pages 232–238, hereinafter Spadaro (1978), and "Electrical Osteogenesis—Role of the Electrode Material" by Spadaro in *Electrical Properties of Bone and Cartilage. Experimental Effects and Clinical Applications*, edited by C. T. Brighton, J. Black, and S. R. Pollack, published by Grune and Stratton, New York, N.Y. 1979, pages 189–192, hereinafter Spadaro (1979), which provide results from potentiostatic studies performed in vitro with electrodes made from cobalt-chrome, gold, platinum, platinum-iridium, silver, tantalum, titanium, as well as stainless-steel with cathodic potentials measured with respect to a saturated, calomel reference electrode. Although not discussed in the above-referenced reports by Spadaro (1978, 1979), each curve exhibits three regions of uniform slope while all curves exhibit two slope changes at two distinct cathodic potentials. Thus, polarization or potentiostatic studies that are performed in vivo with the cathode implanted at the site of desired stimulation and the anode positioned at an appropriate site can be employed to ascertain the initial optimum stimulus for faradic stimulation of osteogenesis. In the first region of the curve of cathodic potential versus the direct current on log scale, substantial osteogenesis is improbable since the microenvironment is not altered significantly by a stimulus in this region. In the third region, osteogenesis occurs but is also accompanied by cellular necrosis, void spaces, and focal coagulation which indicates that a stimulus in this region elicits an osteogenic response either traumatically or with deleterious effects. This form of osteogenic response is generally regarded as reactive bone growth (due to physical and chemical trauma) and not necessarily as bone growth stimulated by the faradic signal which occurs minimally in the first region and maximally in the second region. Finally, optimum faradic stimulation occurs with a stimulus in the second region where osteogenesis occurs in the absence of cellular necrosis, void spaces, or focal coagulation. Within this second region, osteogenesis is increasingly favored as the cathodic potential approaches the transition zone between the second and third regions.

Based upon the last overall conclusion presented above, it would appear that the selection of a faradic stimulus to be used with a particular cathode and anode in specific sites of implantation could be accomplished merely through the performance of a polarization or potentiostatic study which would subsequently permit the identification of an appropriate direct current and cathodic potential near the transition zone between the second and third regions of the resulting curve of the cathodic potential versus the direct current on log scale. However, as first recognized in the above-referenced doctoral dissertation by Baranowski (1983) and then restated in the above-referenced article by Baranowski et al. (1987) on page 412, different types of electrodes, but especially cathodes, to be used in similar implantation sites or even identical electrodes, but again especially cathodes, to be used in different sites would necessitate separate determinations of the stimulus in the manner described above. Furthermore, as later recognized and hereby disclosed by the present inventors, any faradic stimulus based upon initial environmental conditions at the cathode would remain optimal only if such conditions persist over the entire period of faradic stimulation. Thus, a stimulus selected in the above manner would be optimal with a particular cathode and anode in specific implantation sites if, and only if, the period of time necessary to elicit osteogenesis was acute for perhaps no longer than several hours. If, however, the period of stimulation needed to be chronic for more than a day, which is known to be required experimentally in animals and clinically in humans, then the stimulus selected on the basis of a polarization or potentiostatic study performed initially with electrodes surrounded by an unaltered microenvironment would no longer be optimal and may even become detrimental.

Within moments after the initial delivery of a current between cathode and anode, alterations of oxygen tension and pH begin to occur at the cathode due to the reduction reactions involving oxygen consumption plus pH elevation either with or without intermediate hydrogen peroxide formation. These microenvironmental alterations, the same alterations judged to be responsible for stimulation of osteogenesis, result in alterations of the conditions at the cathode surface which affect the electrochemical behavior of the cathode or, essentially, the relationship between the cathodic potential and the direct current. For the curve of cathodic potential versus direct current on log scale, regions of uniform slope and slope changes will still be observed, but the slope of each region and the location of each slope change will change or shift as conditions vary at the cathode surface. This results in a curve that differs over time when compared to one obtained initially with the cathode surrounded by an unaltered microenvironment.

Shifts in the locations of the slope changes due to microenvironmental alterations can be examined by determining how oxygen tension and pH alterations at an in vivo cathode affect the equilibrium potentials. This theoretical examination is possible since the equilibrium and slope change potentials are comparable and, in fact, would be equal if no net current flowed between cathode and anode such that a state of equilibrium prevailed. For the three reactions possible at an in vivo cathode, the theoretical changes in equilibrium or slope change potential due to various alterations in pH and oxygen tension at the cathode surface are as given in Table 1 below. These changes in potential in Table 1 are based on calculations performed with the expressions for the equilibrium potential given in the above-referenced book by Pourbaix (1966) assuming a temperature of 37° C., a pH of 7.4 and an oxygen tension of 50 mm Hg which are all initial conditions typically observed in vivo within medullary canal tissue of long bones. Table 1 was developed by the present inventors and is not considered prior art.

TABLE 1

Theoretical Changes in Equilibrium or Slope Change Potential Due to pH and Oxygen Tension Alterations at the Cathode Surface

| pH at Cathode Surface (pH Unit) | Oxygen Tension at Cathode Surface (mm Hg) | Alteration In pH from Initial In Vivo Conditions (pH Unit) | Alteration In Oxygen Tension from Initial In Vivo Conditions (mm Hg) | Change In Equilibrium or Slope Change Potential (volt) |
|---|---|---|---|---|
| 8.4 | 50 | 1 | 0 | −0.0615[a,b,c] |
| 7.4 | 25 | 0 | 25 | −0.0046[a] or −0.0092[b] |
| 8.4 | 25 | 1 | 25 | −0.0661[a] or −0.0707[b] or −0.0615[c] |

[a]Change in potential for the reaction $O_2 + 2H_2O + 4e^- \rightleftharpoons 4OH^-$
[b]Change in potential for the reaction $O_2 + 2H_2O + 2e^- \rightleftharpoons H_2O_2 + 2OH^-$
[c]Change in potential for the reaction $2H_2O + 2e^- \rightleftharpoons H_2 + 2OH^-$ Referring to Table 1, a pH elevation of one pH unit from a pH of 7.4 to a pH of 8.4, quite probable at the cathode surface, would result in a −0.0615 volt increase in the equilibrium or slope change potentials of all reactions. Like pH, an alteration in oxygen tension can also affect these potentials. A 50 percent depression of oxygen tension from 50 to 25 mm Hg would result in either a −0.0046 or −0.0092 volt increase depending on the reduction reaction. If both a pH elevation of one pH unit and a 50 percent depression of oxygen tension occur, the increase in potential can range from −0.0615 to −0.0707 volt. Overall, significant shifts in the location of the slope changes can be expected as a result of modest alterations of pH and oxygen tension at the cathode surface. However, although the effect of such alterations on equilibrium or slope change potentials can be determined theoretically, the degree to which such alterations occur in vivo cannot be anticipated. Any prediction regarding such alterations from one case to another or even in a single case may be unwarranted since conditions at the cathode may differ initially between cases or at any moment over time. This point is illustrated in FIG. 1 by the scatter of data which was obtained through in vivo polarization studies performed only once, initially, prior to initiation of chronic faradic stimulation, in 13 animal cases bilaterally with identical electrodes in identical implantation sites.

As taught in U.S. Pat. No. 5,056,518 to Pethica et al. on Oct. 15, 1991, tissue impedance and cathode properties may change over time, e.g., with progression of healing. The patent to Pethica et al. identifies a transition or knee of a current-voltage characteristic of an electrode pair used for electrically-induced osteogenesis at which the current increases rather rapidly for small increases in applied voltage. The observation of a large or rapid increase in current for a small increase in potential or voltage signifies that hydrogen gas evolution is occurring at the cathode, as depicted by the third region of the generic curve shown above in FIG. 3. While recognizing the need to adapt for variation in tissue impedance and cathode properties over time, the patent suggests that the operating point should be set beyond the knee of the current-voltage characteristic.

Finally, tissue impedance between cathode and anode, contact impedance at each electrode, and material impedance of each electrode may differ initially between cases and may change over time, as taught, in part, in the above-referenced patent to Pethica et al. These initial differences and temporal changes in various impedances may result in changes and shifts in the curve of cathodic potential versus direct current on log scale. Initial differences and temporal changes in the availability and diffusion of reactants, in particular oxygen, may also occur at each electrode, but especially the cathode, with resulting changes and shifts in the same curve. These differences and changes in the tissue, contact, and material impedances and the availability and diffusion of reactants as well as the initial differences in other environmental conditions between cases and the temporal alterations in microenvironmental conditions at the cathode due to electrochemical reactions as described in detail above, including physical differences in the size, shape, design, composition, and site of implantation or placement of each electrode, among other variables, all influence the electrochemical behavior of the cathode. Therefore, since the electrochemical behavior of the cathode or, more precisely, the existence of electrochemical reactions at the cathode dictates the faradic stimulus to be employed, control of electrochemical reactions would permit optimal faradic stimulation of osteogenesis in each unique case over time.

SUMMARY OF THE INVENTION

It is therefore an object of this present invention to provide a method and apparatus for faradic stimulation of osteogenesis by control of electrochemical reactions, rather than, for example, control of either a constant direct current or a constant cathodic potential.

It is a further object of this present invention to provide an optimal faradic stimulus to be employed with any cathode and anode in any site of implantation or placement in any situation or case for acute or chronic periods, unlike prior art systems such as those with either a constant direct current or a constant cathodic potential where (a) the stimulus must be selected empirically in terms of the magnitudes of the direct current or the cathodic potential for electrodes that differ in material, design, construction, or site of implantation or placement, (b) the stimulus judged optimal in one situation or case may be below or above optimal in another due to differences in initial environmental conditions at the electrodes between situations or cases, and (c) the stimulus may change during chronic use from optimal to non-optimal operation at any moment.

It is a further object of this present invention to provide a method and apparatus for electrochemically controlled faradic stimulation which would be capable of optimal faradic stimulation of osteogenesis with any cathode, or cathodes, and any anode, or anodes, in any site, or sites, of implantation or placement for either acute or chronic time periods. A system based on this present invention would be consistently optimal because the stimulation would be controlled by the electrochemical behavior exhibited by the cathode. Such a system would permit delivery of a safe, efficacious, and optimal electrical signal to stimulate osteogenesis at any suitable tissue site in living tissue.

It is a further object of this present invention to achieve electrochemically controlled faradic stimulation of osteogenesis through maintenance of a stimulus yielding the maximum acceptable level of oxygen consumption and pH elevation at the cathode, either with or without the formation of hydrogen peroxide as only an intermediate chemical species, while preventing the initiation of hydrogen gas evolution. A system based on this present invention would maintain electrochemical reactions resulting in depression of oxygen tension plus elevation of pH, environmental effects that favor osteogenesis, and prevent a reaction resulting in elevation of pH plus hydrogen gas evolution, the latter effect being detrimental.

The above and other objects are achieved in accordance with the preferred embodiments of this present invention through an overall process of data acquisition, data analysis, stimulus initiation, and stimulus adjustment. Data involving either the environmental conditions at the electrodes and electrical conditions of the electrodes or only the electrical conditions of the electrodes, depending on the preferred embodiment, is acquired initially prior to stimulus initiation. The above acquired data are appropriately analyzed and the faradic stimulus is then initiated. On a periodic basis throughout the period of stimulation, the above data are acquired and, based upon its analysis, the stimulus is adjusted through closed-loop feedback control in order to maintain only electrochemical reactions beneficial to the stimulation of osteogenesis while preventing any electrochemical reaction detrimental to the same at the site of desired osteogenesis. This overall process therefore maintains reactions resulting in depression of oxygen tension plus elevation of pH, effects that favor osteogenesis, and prevents a reaction resulting in elevation of pH plus hydrogen gas evolution, the latter effect being detrimental. In terms of the electrochemical behavior of the cathode as exemplified by the curve of the cathodic potential versus direct current on log scale as shown generically in FIG. 3, the overall process described above results consistently in a direct current and cathodic potential, neither quantity being maintained constant chronically, at or below, but not above or beyond, the transition zone between the second and third regions. The stimulus is maintained at or below, but not above or beyond, said transition zone despite changes or shifts in the regions of uniform slope or the location of slope changes.

The above and other objects of this present invention are based on the theory that a faradic stimulus acts on cells through alterations of the microenvironment as a result of electrochemical reactions. This theory is believed to be the dominant mechanism by which a faradic stimulus elicits osteogenesis at the cathode. Cation migration to the cathode, electrode trauma, electrode micromotion, and other effects in the absence of electrochemical reactions, including effects on cells by electric fields or ion fluxes, may also be operative either acutely or chronically during faradic stimulation of osteogenesis. However, although these effects may contribute to an osteogenic response, they are judged to play a less influential role in faradic stimulation when microenvironmental alterations are possible. In fact, microenvironmental alterations as a result of electrochemical reactions are deemed sufficient to explain the effects of faradic stimulation on osseous tissue in the vast majority of reported experimental studies in animals and clinical cases in humans.

Further objects, advantages, and novel features of this present invention will become apparent from the following detailed description of the preferred embodiments when considered in conjunction with the accompanying drawings.

DESCRIPTION OF THE PREFERRED EMBODIMENTS

For the purposes of promoting an understanding of the principles of this present invention, reference will now be made to the preferred embodiments in conjunction with the drawings and specific language will be used to described the same. It will nevertheless be understood that no limitation of the scope of this invention is thereby intended, and that alterations and further modifications to the described method and illustrated apparatus as well as further applications of the principles of this present invention as described and illustrated herein are contemplated as would normally occur to one skilled in the art to which this present invention relates.

Figure 3:
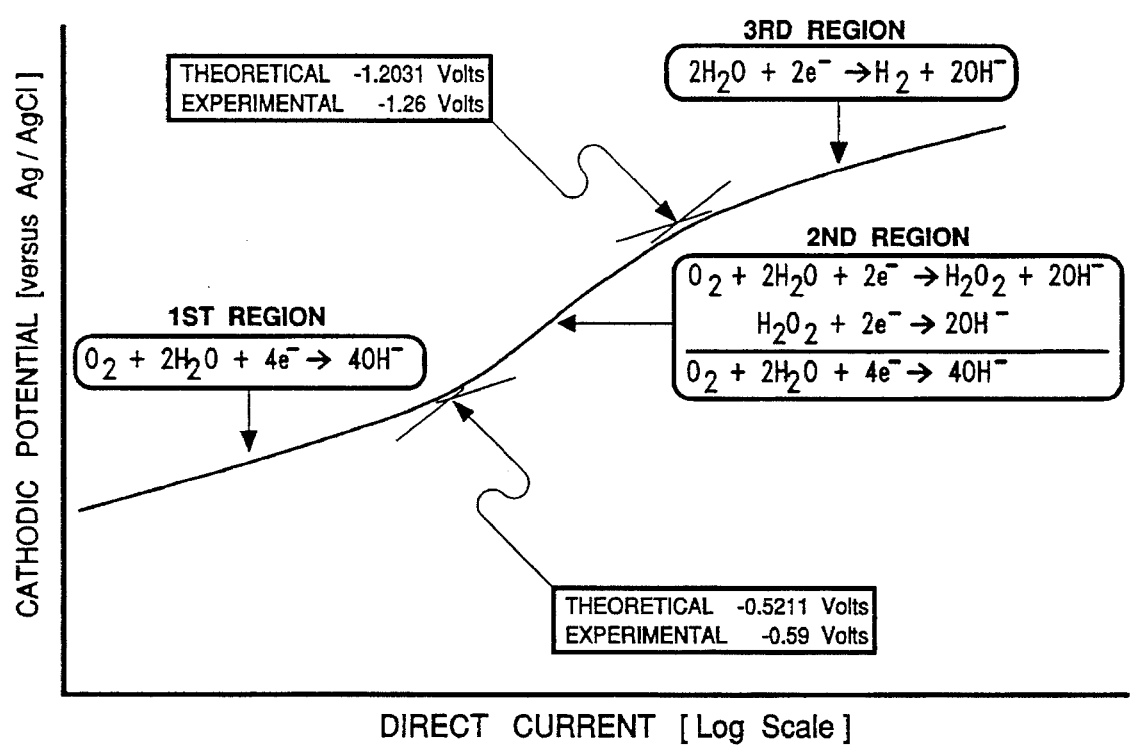
FIG. 3 is a generic curve relating the cathodic potential to the log of the direct current with a reduction reaction or process indicated for each of its three regions.

Electrochemically controlled faradic stimulation of osteogenesis would involve the maintenance of a stimulus yielding the maximum level of intermediate hydrogen peroxide formation, oxygen consumption, and pH elevation at the cathode while preventing the initiation of hydrogen gas evolution. In terms of the curve of the cathodic potential versus the direct current on log scale as shown generically in FIG. 3, the stimulus would consistently result in a direct current and cathodic potential at or below, but not above or beyond as taught in the above-referenced patent by Pethica (1991), the transition zone between the second and third regions despite changes or shifts in the regions of uniform slope or the location of slope changes. On the assumption that microenvironmental alterations of oxygen tension and pH due to electrochemical reactions are sufficient to elicit the biological response to a faradic stimulus, faradic stimulation by control of electrochemical reactions would be consistently optimal with any electrodes in any site of implantation or placement for either acute or chronic time periods because the stimulus would be controlled by the electrochemical behavior of the cathode.

Figure 1:
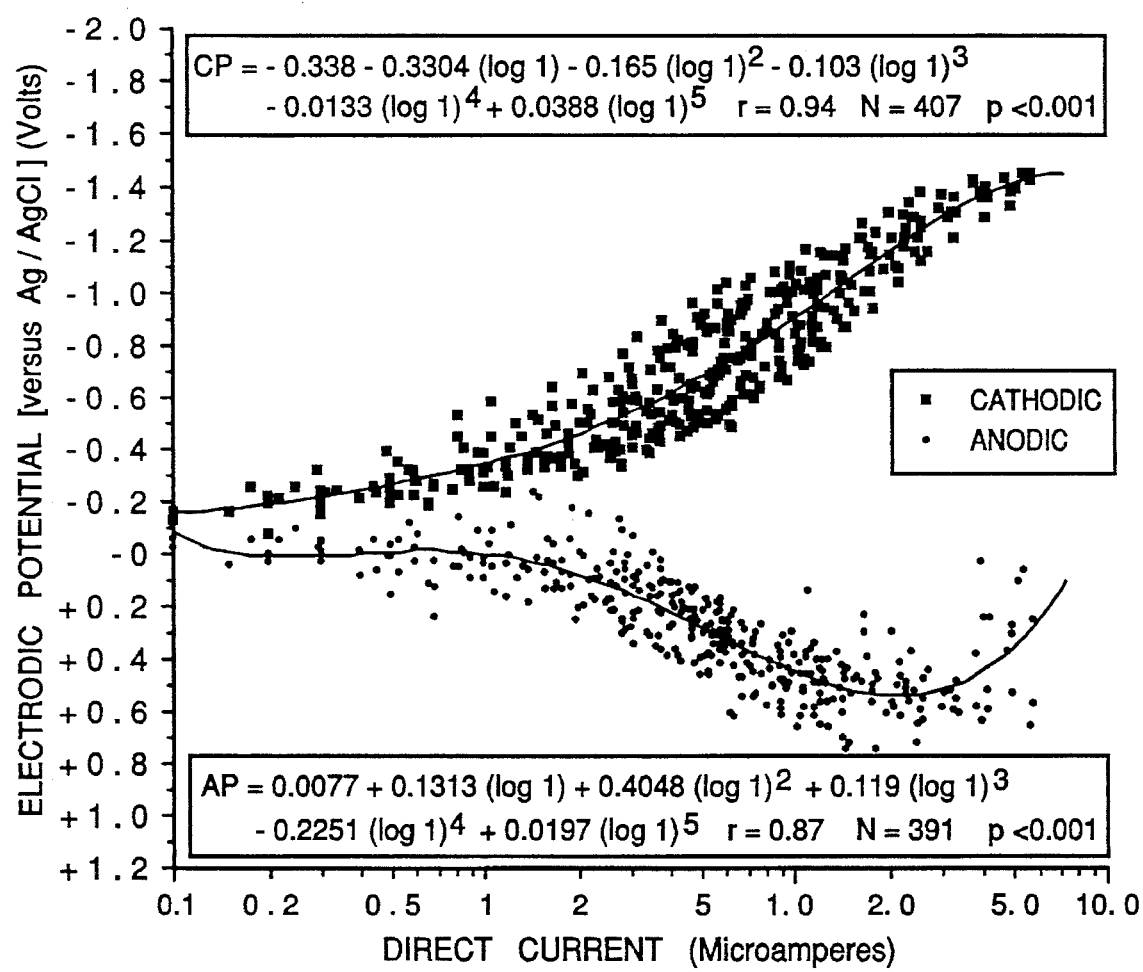
FIG. 1 is a plot of electrodic potentials versus direct current on log scale obtained from polarization studies performed in vivo.
Figure 2:
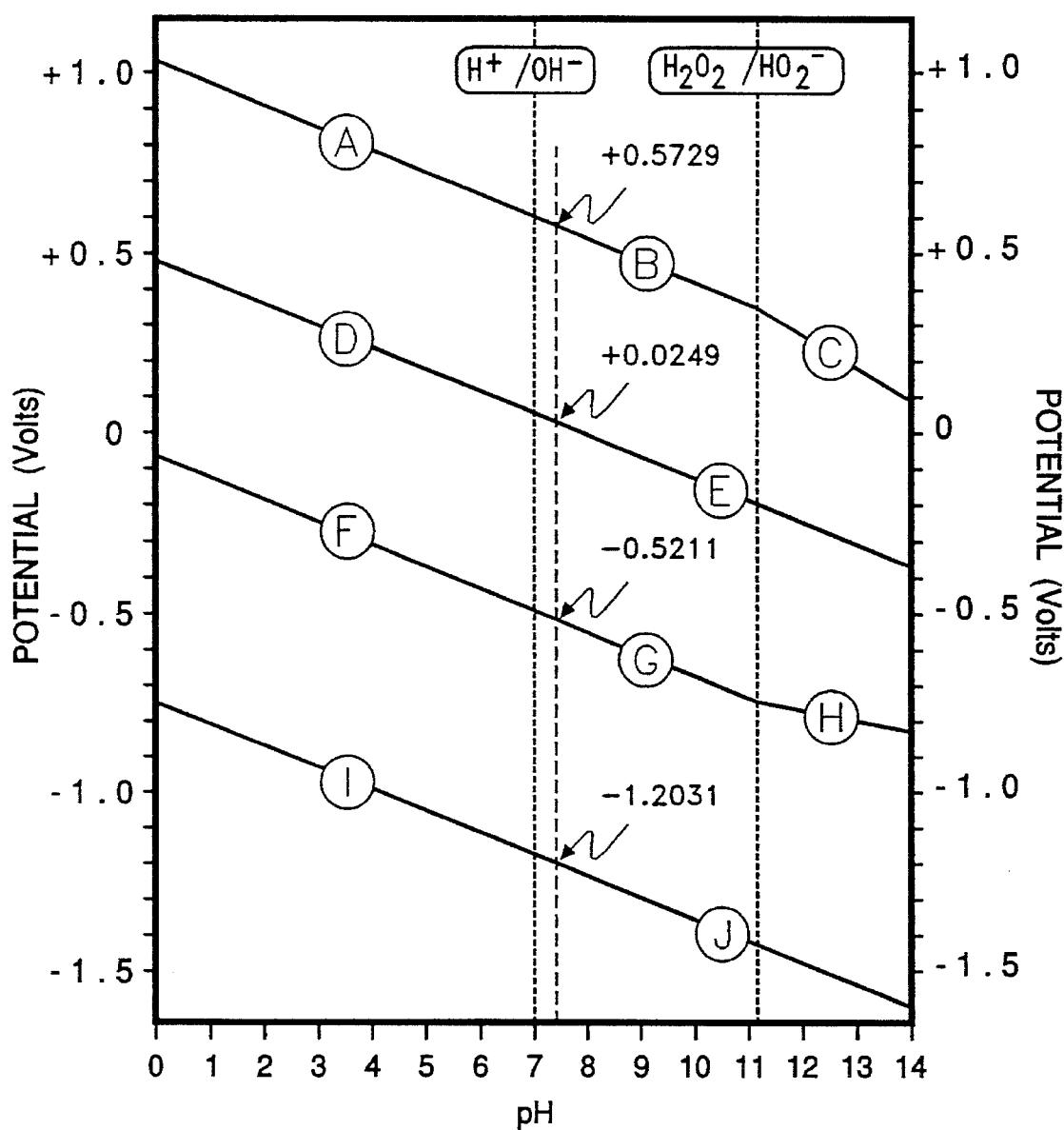
FIG. 2 is a potential versus pH diagram for reactions involving water, oxygen, hydrogen, hydrogen ion, hydroxyl ion, hydrogen peroxide, and hydrogen peroxide ion at an in vivo temperature of 37° C. with respect to an Ag/AgCl reference electrode in a 0.1 molar solution of chloride ions at an in vivo temperature of 37° C. and an in vivo pH of 7.40.
Figure 4A:
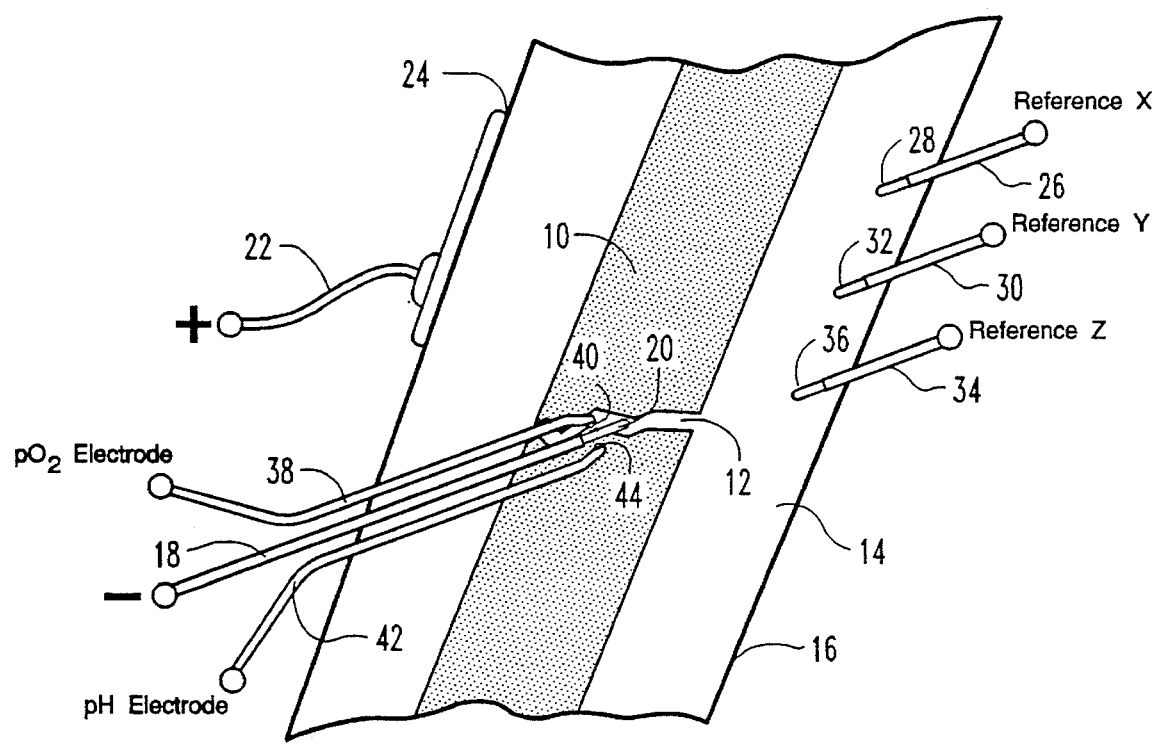
FIG. 4A is a side representational view of an electrode arrangement according to a first embodiment of the present invention.

Suitable for use in this present invention, a system of electrodes is depicted in FIG. 4A for faradic stimulation in bone 10 that requires osteogenesis for repair at tissue site 12 which is surrounded by muscle or other subcutaneous tissue 14 covered by skin 16. As required electrodes, a cathode 18 is positioned such that its conductive exposure or port 20 is in the vicinity of or at tissue site 12 where osteogenesis is desired while an anode 22 is positioned such that its conductive exposure 24 is distant from tissue site 12 in muscle or other subcutaneous tissue 14 or on skin 16. The term "port" is typically employed to described a site of conductive exposure on, specifically, the cathode 18, as originally presented in the above-referenced article by Black et al. (1979). The cathode 18 may be totally implanted, percutaneous, or specifically in the oral cavity, topical provided that its conductive exposure or port 20 is placed in the vicinity of or at tissue site 12 where osteogenesis is desired. The anode 22 may be totally implanted, percutaneous, or topical provided that its conductive exposure 24 is placed distant to tissue site 12. The cathode 18 and anode 22 may be constructed from stainless-steel, titanium, platinum, platinum alloy, or other metallic material or other conductive, non-metallic material and may include insulation constructed from polytetrafluoroethylene, silicone rubber, or other non-conductive material provided that all materials are biocompatible where a biocompatible material means a material that exhibits an acceptable, acute and chronic local tissue response. The functional part of each electrode is the conductive exposure or, specifically for the cathode 18, the port with controlled geometry to produce typical current densities and potentials gradients, as described in the above-referenced article by Black et al. (1979). Specifications for effective size, shape, and design of the cathode 18 and its conductive exposure or port 20 are provided in the above-referenced article by Black et al. (1979), although this present invention is not limited to any particular size, shape, or design of either electrode or its conductive exposure or port. Furthermore, although a single cathode and anode, each having a single conductive exposure or port, are depicted in FIG. 1, this present invention is not limited to a particular number of cathodes, anodes, or conductive exposures or ports on each electrode.

In cases where anode 22 is not different, as will be explained, a reference electrode 26, also identified as "Reference X", is positioned such that its conductive exposure 28 is distant from tissue site 12 in muscle or other subcutaneous tissue 14 or on skin 16 to permit measurement of electrodic potentials. In a first embodiment of the invention, an oxygen tension electrode 38 is positioned such that its oxygen sensitive exposure 40 is in the vicinity of or at the conductive exposure or port 20 of the cathode 18 while, in combination with the oxygen tension electrode 38, a reference electrode 30, also identified as "Reference Y", is positioned such that its conductive exposure 32 is distant from tissue site 12 in muscle or other subcutaneous tissue 14 or on skin 16 to permit measurement of oxygen tension, and a pH electrode 42 is positioned such that its hydrogen ion sensitive exposure 44 is in the vicinity of or at the conductive exposure or port 20 of the cathode 18 while, in combination with the pH electrode 42, a reference electrode 34, also identified as "Reference Z", is positioned such that its conductive exposure 36 is distant from tissue site 12 in muscle or other subcutaneous tissue 14 or on skin 16 to permit measurement of pH. The three reference electrodes 26, 30, and 34 are involved in the performance of different measurements and, for this reason, have been identified with the labels "Reference X", "Reference Y", and "Reference Z" in FIG. 4, although said three electrodes may be identical. Each of the three reference electrodes 26, 30, and 34 may be totally implanted, percutaneous, or even topical provided that the conductive exposure of each reference electrode is placed distant to tissue site 12. The oxygen tension electrode 38 and the pH electrode 42 may be totally implanted, percutaneous, or, specifically in the oral cavity, even topical provided that the exposure of each electrode is placed in the vicinity of or at the conductive exposure or port 20 of the cathode 18. Each of the three reference electrodes 26, 30, and 34 may be constructed from a silver substrate coated with silver chloride, hereinafter referred to as "Ag/AgCl", or other conductive material or combination of materials and may include insulation constructed from polytetrafluoroethylene, silicone rubber, or other non-conductive material provided that all materials are biocompatible and produce an electrode that is reversible or nonpolarizable where a reversible or nonpolarizable electrode means a electrode that can pass current without changing the chemical environment in its vicinity. The oxygen tension electrode 38 may be constructed from gold, platinum, silver, or other conductive material and may include insulation constructed from polytetrafluoroethylene, silicone rubber, or other non-conductive material to produce a oxygen sensitive exposure 40 which may be coated, if necessary to prevent attachment of biological substances and, thus, prevent reduced sensitivity to oxygen, by glass, polypropylene, polytetrafluoroethylene, or other material that is selectively permeable to oxygen provided that all materials are biocompatible. The pH electrode 42 may be constructed from Ag/AgCl, antimony, platinum, or other conductive material immersed in appropriate ionic solution surrounded by glass or other material that is selectively permeable to hydrogen ion and may include insulation constructed from polytetrafluoroethylene, silicone rubber, or other non-conductive material to produce a hydrogen ion sensitive exposure 44 provided that all materials are biocompatible. Specifications for size, shape, and design of the three reference electrodes 26, 30, and 34, the oxygen tension electrode 38, the pH electrode 42, and the exposure of these various electrodes are provided in the above-referenced doctoral dissertation by Baranowski (1983), although this present invention is not limited to any particular size, shape, or design of these various electrodes or their exposure.

A first embodiment of this present invention involves oxygen tension and pH measurements at the cathode. These measurements would be performed using either (a) an oxygen tension electrode 38 and a pH electrode 42, each in combination with its reference electrode 30 and 34 or (b) the cathode 18 or some portion thereof in combination with a reference electrode 30 or 34 provided that cathode 18 is constructed from material or materials permitting oxygen tension and pH measurements to be performed. Measurements of direct current between cathode 18 and anode 22, hereinafter referred to as "direct current" unless otherwise noted; interelectrode potential between cathode 18 and anode 22, hereinafter referred to as "interelectrode potential"; cathodic potential between cathode 18 and reference electrode 26, hereinafter referred to as "cathodic potential"; as well as anodic potential between anode 22 and reference electrode 26, hereinafter referred to as "anodic potential", would also be obtained. Data from the measurements of environmental conditions at the cathode 18 and electrical conditions of the cathode 18 and anode 22 would be acquired prior to initiation of any stimulus to ascertain initial conditions and, thus, identify differences in initial conditions between cases or situations. Said data would be appropriately analyzed using developed algorithms which may include, but may not be limited to, pertinent factors and expressions involving oxygen tension, pH the relationships among oxygen tension, pH, and equilibrium potentials of electrochemical reactions, and the rates of oxygen consumption and pH elevation which are both dictated by the magnitude of direct current. Based upon said analysis, faradic stimulation would then be initiated by applying an interelectrode potential that is permitted to vary in order to result in a constant cathodic potential. The constant cathodic potential would be minimal in magnitude initially and, unlike a constant direct current where the cathodic potential is permitted to vary, would dictate the type of electrochemical reaction at the cathode 18 and, thereby, prevent a change in said type.

On a periodic basis throughout the stimulation period, perhaps several times daily, the above data would be acquired upon temporary interruption of the faradic stimulus and, based upon its analysis, the constant cathodic potential stimulus would be adjusted to maintain only electrochemical reactions beneficial to the stimulation of osteogenesis while preventing any reaction detrimental to the same at, in both cases, the cathode 18, the site of desired osteogenesis. Furthermore, said stimulus would be adjusted to account for temporal changes in conditions at the cathode 18 so that the reactions resulting in depression of oxygen tension plus elevation of pH, the effects that favor osteogenesis, would be maintained at maximum acceptable levels while the reaction resulting in elevation of pH plus hydrogen gas evolution, the latter effect being detrimental, would be prevented. The constant cathodic potential stimulus would only be chronic at a set magnitude between adjustments, not throughout the stimulation period. Adjustment of said stimulus is preferably made automatically, although manual adjustment would be adequate in certain cases or situations. Suitable for use in this first preferred embodiment of this present invention, a faradic device to accomplish the overall process of data acquisition, data analysis, stimulus initiation, and stimulus adjustment will be described in detail later.

Figure 4B:
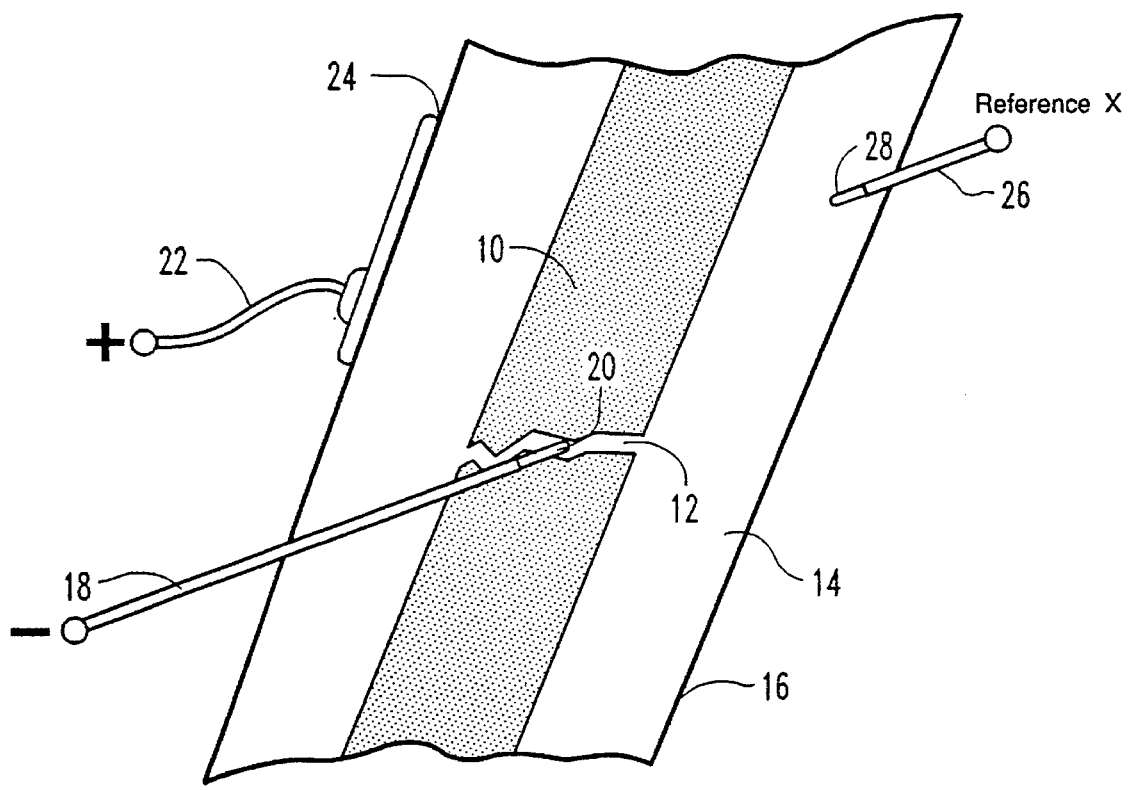
FIG. 4B is a side representational view of an electrode arrangement according to second and third embodiments of the present invention.

A second, more preferred embodiment of this present invention involves polarization or potentiostatic studies with the electrodes shown in FIG. 4B, wherein like numbers and letters appear for elements like those of FIG. 4A. The electrochemical behavior of the cathode, as exemplified by the curve of the cathodic potential versus direct current on log scale, hereinafter referred to as "cathodic potential curve", would be ascertained by performing either (a) a polarization study where a controlled interelectrode potential that increases over time is applied while measurements are made of the resultant direct current, cathodic potential, and anodic potential or (b) a potentiostatic study where an interelectrode potential that increases over time is applied but is permitted to vary in order to result in a controlled cathodic potential while measurements are made of the resultant direct current, interelectrode potential, and anodic potential. Data from the polarization or potentiostatic study would be acquired prior to initiation of any stimulus to ascertain initial conditions and, thus, identify differences in initial conditions between cases or situations. With either study, the interelectrode potential would be adjusted or scanned over a range from zero (0) volt, or some other minimum potential, to a potential which results in the identification of the transition zone between the second and third regions of the cathodic potential curve. Said transition zone would be identified from appropriate analysis of the acquired data using developed algorithms which may include, but may not be limited to, graphic interpretations and linear, polynomial, and exponential regressions of the cathodic potential curve. Once said transition zone is identified upon the above analysis, the polarization or potentiostatic study would be terminated to prevent any further increase in cathodic potential. Said termination would prevent any advance above or beyond said transition zone into the third region of the cathodic potential curve and, thus, prevent any possibility of hydrogen gas evolution at the cathode 18. Faradic stimulation would then be initiated by maintaining an interelectrode potential that is permitted to vary in order to result in a constant cathodic potential.

On a periodic basis throughout the stimulation period, perhaps several times daily, a polarization or potentiostatic study would be performed anew upon temporary interruption of the faradic stimulus, the above data would be acquired and analyzed, and, based upon the data analysis, the constant cathodic potential stimulus would be adjusted to remain at or below, but not above or beyond, the transition zone between the second and third regions of the cathodic potential curve. Adjustment of said stimulus would maintain only electrochemical reactions beneficial to the stimulation of osteogenesis while preventing any reaction detrimental to the same at, in both cases, the cathode 18, the site of desired osteogenesis. Furthermore, said stimulus would be adjusted to account for temporal changes in conditions at the cathode 18 so that the reactions resulting in depression of oxygen tension plus elevation of pH, the effects that favor osteogenesis, would be maintained at maximum acceptable levels while the reaction resulting in elevation of pH plus hydrogen gas evolution, the latter effect being detrimental, would be prevented. The constant cathodic potential stimulus would only be chronic at a set magnitude between adjustments, not throughout the stimulation period. Adjustment of said stimulus is preferably made automatically, although manual adjustment would be adequate in certain cases or situations. Identification of the transition zone between the second and third regions of the cathodic potential curve may also be obtained from the curve of the interelectrode potential versus direct current on log scale, hereinafter referred to as "interelectrode potential curve". Identification of said transition zone from the interelectrode potential curve is possible if, and only if, the anode 22 is indifferent where an indifferent anode means an anode 22 much larger in surface area than the cathode 18 such that the anode 22 would exhibit a very small anodic potential despite even a large direct current. Use of an anode 22 that is indifferent would result in an interelectrode potential curve that is only slightly offset in potential from a cathodic potential curve. Use of an anode 22 that is indifferent would permit a constant interelectrode potential, rather than a constant cathodic potential, stimulus to be employed initially and between stimulus adjustments and would also eliminate the need for measurement of the cathodic potential. Thus, a reference electrode 26 is not required if the anode 22 is indifferent. Suitable for use in this second preferred embodiment of this present invention, a faradic device to accomplish the overall process of data acquisition, data analysis, stimulus initiation, and stimulus adjustment will be described in detail later.

The third and most preferred embodiment of this present invention also involves polarization or potentiostatic studies with the electrodes shown in FIG. 4B, like the second, more preferred embodiment presented above, but with a different analysis of the acquired data. The electrochemical behavior of the cathode, as exemplified by the cathodic potential curve, would still be ascertained by performing either a polarization or potentiostatic study as described in detail above. Data from the polarization or potentiostatic study would again be acquired prior to initiation of any stimulus to ascertain initial conditions and, thus, identify differences in initial conditions between cases or situations. With either study, the interelectrode potential would still be adjusted or scanned over a range from zero (0) volt, or some other minimum potential, to a potential which results in the identification of the transition zone between the second and third regions of the cathodic potential curve. However, unlike the second, more preferred embodiment presented above, said transition zone would be identified from appropriate analysis of the acquired data using developed algorithms which may include, but may not be limited to, mathematical calculations of (a) the change in direct current with respect to the change in cathodic potential or, essentially, the inverse slope of the cathodic potential curve and (b) the change in direct current with respect to the square of the change in cathodic potential or, essentially, the change in inverse slope of the cathodic potential curve. Note that the term "slope" is defined mathematically as the change in ordinate or y-axis data with respect to a change in abscissa or x-axis data and, for this reason, the phrase "inverse slope" is defined here as a change in abscissa or x-axis data with respect to a change in ordinate or y-axis data, essentially the inverse of slope. Once said transition zone is identified upon the above analysis, the polarization or potentiostatic study would be terminated to prevent any further increase in cathodic potential. Said termination would prevent any advance above or beyond said transition zone into the third region of the cathodic potential curve and, thus, prevent any possibility of hydrogen gas evolution at the cathode 18. Faradic stimulation would then be initiated by maintaining an interelectrode potential that is permitted to vary in order to result in a constant cathodic potential.

On a periodic basis throughout the stimulation period, perhaps several times daily, a polarization or potentiostatic study would be performed anew upon temporary interruption of the stimulus, the above data would be acquired and analyzed, and, based upon the data analysis, the constant cathodic potential stimulus would be adjusted to remain at or below, but not above or beyond, the transition zone between the second and third regions of the cathodic potential curve. Adjustment of said stimulus would maintain only electrochemical reactions beneficial to the stimulation of osteogenesis while preventing any reaction detrimental to the same at, in both cases, the cathode 18, the site of desired osteogenesis. Furthermore, said stimulus would be adjusted to account for temporal changes in conditions at the cathode 18 so that the reactions resulting in depression of oxygen tension plus elevation of pH, the effects that favor osteogenesis, would be maintained at maximum acceptable levels while the reaction resulting in elevation of pH plus hydrogen gas evolution, the latter effect being detrimental, would be prevented. The constant cathodic potential stimulus would only be chronic at a set magnitude between adjustments, not throughout the stimulation period. Adjustment of said stimulus is preferably made automatically, although manual adjustment would be adequate in certain cases or situations.

Identification of the transition zone between the second and third regions of the cathodic potential curve may also be obtained from the interelectrode potential curve if, and only if, the anode 22 is different such that the interelectrode potential curve is only slightly offset in potential from a cathodic potential curve. Said transition zone from the interelectrode potential curve would then be identified from appropriate analysis of the acquired data using developed algorithms which may include, but may not be limited to, mathematical calculations of (a) the change in direct current with respect to the change in interelectrode potential or, essentially, the inverse slope of the interelectrode potential curve and (b) the change in direct current with respect to the square of the change in interelectrode potential or, essentially, the change in inverse slope of the interelectrode potential curve. As discussed above, use of an anode 22 that is indifferent would permit a constant interelectrode potential, rather than a constant cathodic potential, stimulus to be employed initially and between stimulus adjustments and would also eliminate the need for measurement of the cathodic potential. Thus, a reference electrode 26 would not be required. Suitable for use in this third and most preferred embodiment of this present invention, a faradic device to accomplish the overall process of data acquisition, data analysis, stimulus initiation, and stimulus adjustment will be described in detail later.

Figure 5:
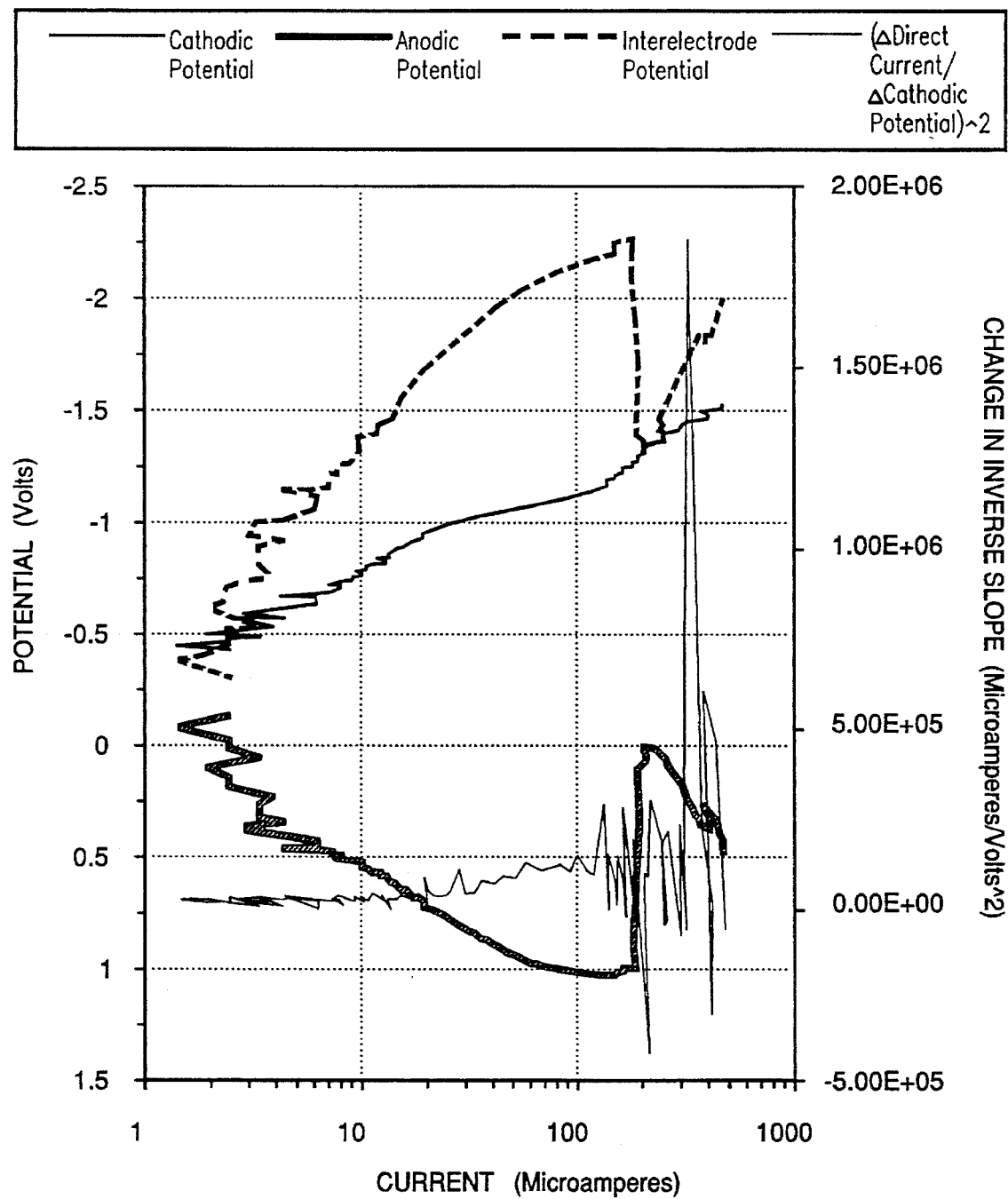
FIG. 5 is a plot of cathodic, anodic, and interelectrode potentials plus the change in current with respect to the square of the change in cathodic potential versus the direct current on log scale obtained from a potentiostatic study performed in vitro with electrodes typically employed in vivo for faradic stimulation of osteogenesis.
Figure 6:
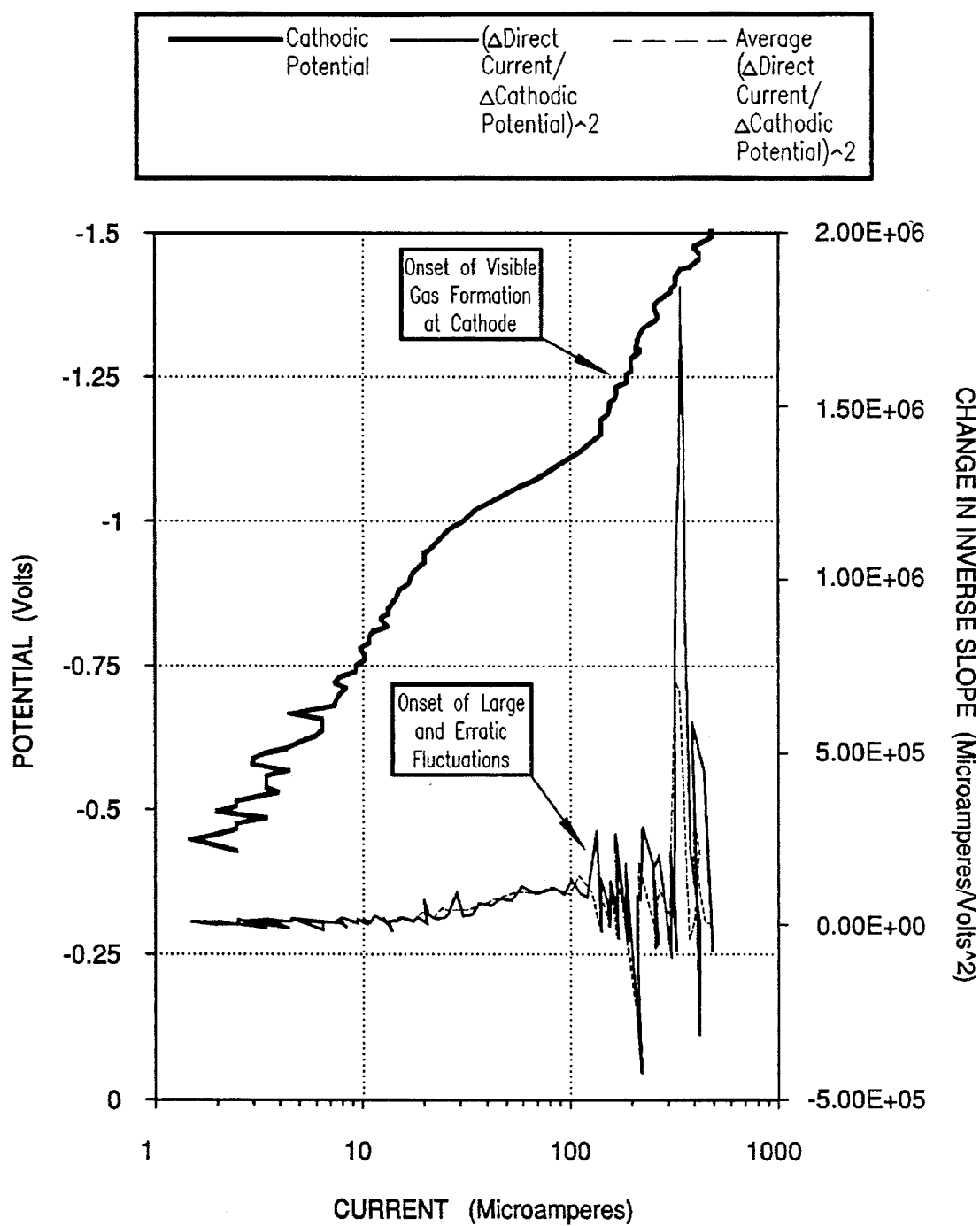
FIG. 6 is a plot of cathodic potential plus change in current with respect to the square of the change in cathodic potential, as raw and three-pointed averaged data, versus the direct current on log scale with the onset of visible gas formation at the cathode in vitro following the onset of large and erratic fluctuations in the curve of the change in direct current with respect to the square of the change in cathodic potential versus the direct current on log scale.

Identification of the transition zone between the second and third regions of the cathodic potential curve according to the third embodiment described above, has been accomplished by the inventors of this present invention on data collected previously from potentiostatic studies performed in vitro with electrodes typically employed in faradic stimulation of osteogenesis in vivo. FIG. 5 is a plot of the cathodic, anodic, and interelectrode potentials versus direct current on log scale plus the results of a mathematical analysis involving the calculation of the change in direct current with respect to the square of the change in cathodic potential or, essentially, the change in inverse slope of the cathodic potential curve. FIG. 6 is a rescaled version of the plot given in FIG. 5 with the curves involving anodic and interelectrode potentials deleted for clarity and with the change in inverse slope of the cathodic potential curve presented in raw and three-point averaged forms. In both figures, the onset of large and erratic fluctuations in the curve of the change in inverse slope of the cathodic potential curve precedes the onset of gas evolution at the cathode 18 that can be observed in vitro. Because the onset of gas evolution at the cathode 18 indicates the end of the transition zone between the second and third regions of the cathodic potential curve, identification of said transition zone prior to the onset of gas evolution is now possible according to the third and most preferred embodiment of this present invention. Thus, by identifying said transition zone prior to the onset of gas evolution at the cathode 18, optimization of faradic stimulation of osteogenesis according to this present invention is now possible by control of electrochemical reactions through maintenance of a stimulus yielding the maximum acceptable level of oxygen consumption and pH elevation, either with or without the formation of hydrogen peroxide as only an intermediate chemical species, while preventing the initiation of gas evolution at, in both cases, the cathode 18, the site of desired osteogenesis.

Figure 7A:
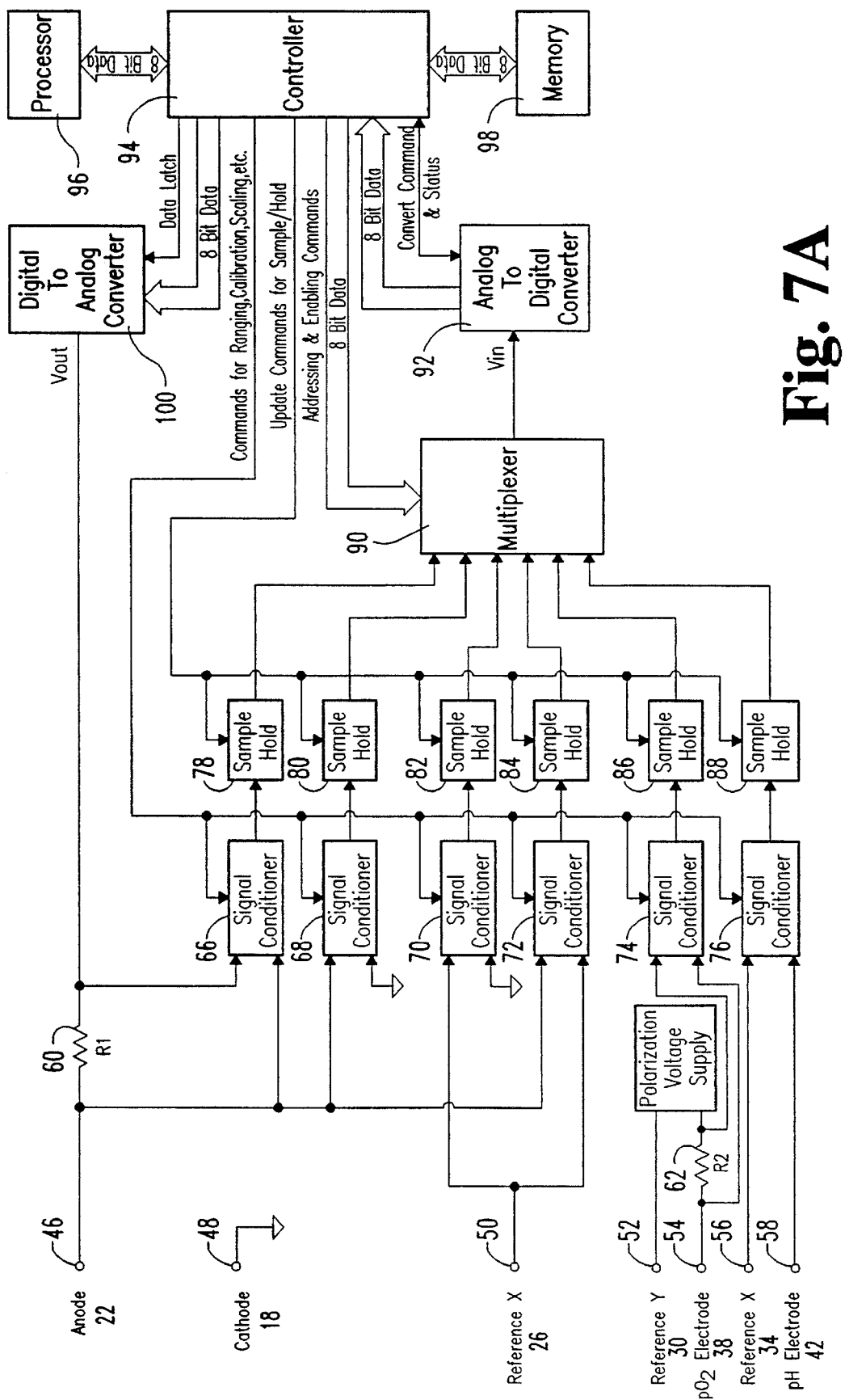
FIG. 7A is a block diagram of a faradic device for stimulation of osteogenesis according to the first embodiment of the present invention.
Figure 7B:
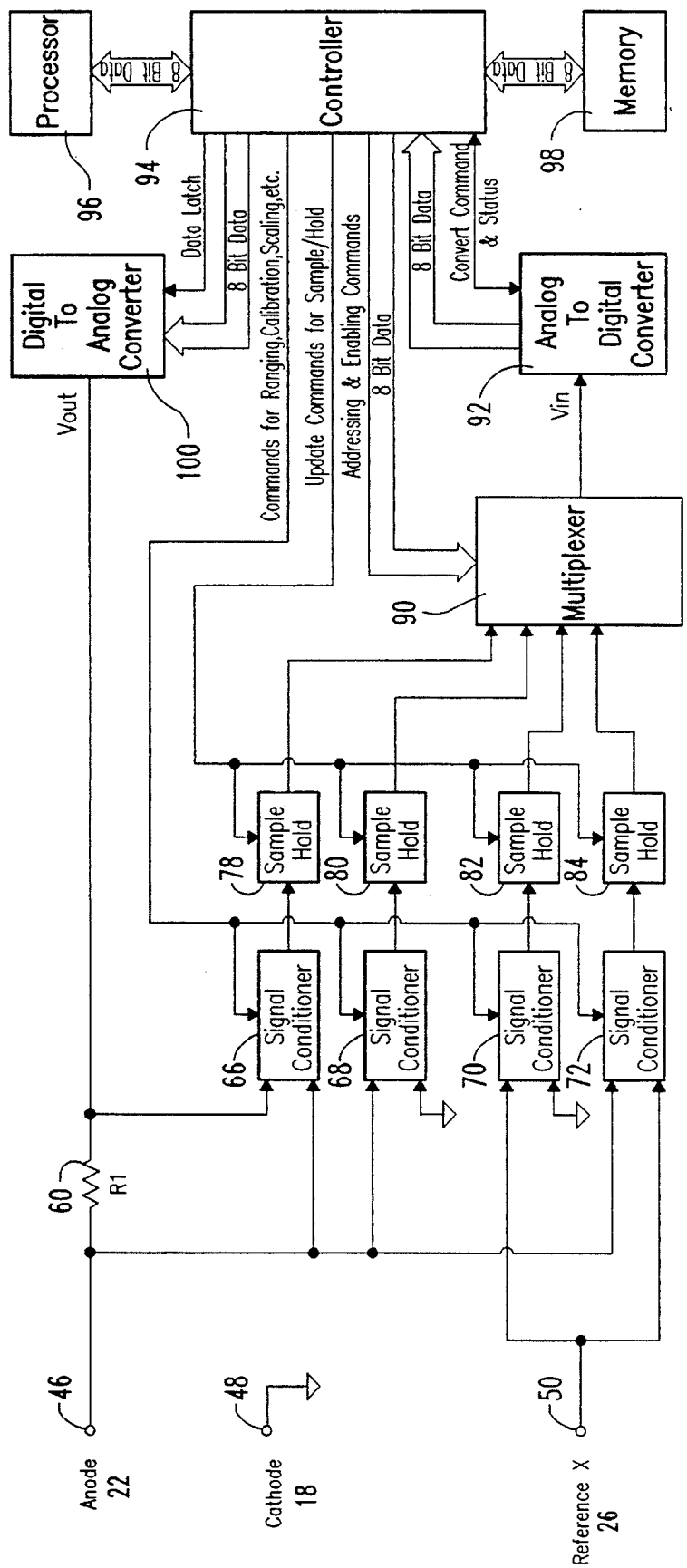
FIG. 7B is a block diagram of a faradic device for stimulation of osteogenesis according to the second and third embodiments of the present invention.

A faradic device for stimulation of osteogenesis according to the first embodiment of this present invention is illustrated by block diagram in FIG. 7A and a corresponding device according to the second and third embodiments of this invention is illustrated in the block diagram of FIG. 7B. It will be understood that the electrode hardware of FIG. 7A could also perform as the second and third embodiment of this invention if desired, with the circuitry for the $pO_2$ and pH electrodes disabled, but the second and third embodiment circuitry is shown separately in FIG. 7B for purposes of clarity. Numbers and labels identical to those in FIGS. 4A and 4B represent like elements throughout FIGS. 7A and 7B, respectively. An anode contact 46 and a cathode contact 48 are provided for physical connection or some other coupling method to, respectively, the anode 22 and the cathode 18. Contacts 50, 52, 56, 54, and 58 are provided for physical connection or other coupling method to, respectively, the three reference electrodes 26, 30, 34, the oxygen tension electrode 38, and the pH electrode 42. The device shown in FIG. 7A is capable of acquiring the following analog input data or signals, each as a potential or voltage:

(A) direct current between cathode 18 and anode 22 via the potential drop across a resistor 60, also identified with label "R1", in series with cathode 18;

(B) interelectrode potential between cathode 18 and anode 22;

(C) cathodic potential between cathode 18 and Reference X 26;

(D) anodic potential between anode 22 and Reference X 26;

(E) oxygen tension from the current, produced upon polarization using polarization voltage supply 64, between $pO_2$ Electrode 38 and Reference Y 30 via the potential drop across a resistor 62, also identified with label "R2", in series with $pO_2$ Electrode 38; and, finally, (F) pH from the potential between pH Electrode 42 and Reference Z 34.

Still referring to FIGS. 7A and 7B, the major components of said device and their functions are as follows. Distinct signal conditioners 66, 68, 70 and 72 and, in the case of the first embodiment, signal conditioners 74 and 76, are provided for conditioning and preparation of the above analog input data, including ranging, calibration, scaling, amplification, and filtering as appropriate. Distinct sample/holds 78, 80, 82, 84, 86, and 88 (sample holds 86 and 88 for first embodiment only) are provided for rapid, even simultaneous, acquisition of the above analog input data or signals such that said data or signals delineating the environmental conditions at the cathode 18 and the electrical conditions of the cathode 18 and the anode 22 can be acquired at the same given instant. A multiplexer 90 is provided for sequential or random selection of one or more of the above analog input data or signals. An analog-to-digital converter 92 is provided to receive the selected analog input data or signal from the multiplexer 90 for conversion from analog to digital format. A controller 94 with an internal clock or timer is provided to (a) generate the commands to the signal conditioners 66, 68, 70, 72, 74, and 76 for conditioning and preparation of the above analog input data or signals; (b) generate the commands to the sample/holds 78, 80, 82, 84, 86, and 88 for timing of the acquisition of the above analog input data or signals; (c) generate the commands to the multiplexer 90 for selection of one or more of the above analog input data or signals; (d) generate the commands to the analog-to-converter 92 for conversion of the above analog input data or signals from analog to digital format; (e) receive the digital input data or signals from the analog-to-converter 92; (f) send the digital input data or signals from the analog-to-converter 92 to the processor 96 and the memory 98; (g) receive the processed digital output data or signal from the processor 96; and, finally, (h) send the processed digital output data or signal from the processor 96 to the memory 98 and the digital-to-analog converter 100 via data latch command. A processor 98, controlled by software, is provided to rapidly, at times almost simultaneously, (a) receive the digital input data or signals from the controller 94; (b) process the digital input data or signals by appropriate analysis to be described in detail below; and (c) send the processed digital output data or signal back to the controller 94 so that the controller 94 can send the processed digital output data or signal to the memory 98 and the digital-to-analog converter 100. A memory 98 is provided to receive and send the unprocessed digital input data or signals and the processed digital output data or signal from and to the controller 94 as well as store all said data or signals to permit review upon retrieval or transfer. A digital-to-analog converter 100 is provided to receive the processed digital output data or signal from the controller 94 for conversion from digital to analog format and then apply the appropriate analog output data or signal as a potential or voltage, via closed-loop feedback control, between the anode contact 46 and, thus, the anode 22 and, given the internal ground, the cathode contact 48 and, thus, the cathode 18.

Initially, prior to the initiation of any stimulus, the analog input data or signals that are required according to the first, second, or third preferred embodiment described above would be conditioned and prepared, selected, and converted from analog to digital format by the combination of the signal conditioner 66, 68, 70, 72, 74, or 76, the sample/hold 78, 80, 82, 84, 86, or 88, as appropriate for the embodiment, the multiplexer 90, and the analog-to-digital converter 93 which are all controlled by various commands from the controller 94. The digital input data or signals would be transferred as necessary by the controller 94 to the processor 96 and the memory 98. After processing, the digital output data or signal would be transferred from the processor back to the controller 94 where said data or signal would then be transferred to the memory 98 and the digital-to-analog converter 100. The digital output data or signal would be converted from digital to analog format by the digital to analog converter 100 so that the appropriate analog output data or signal as a potential or voltage can be applied, via closed-loop feedback control, between the anode contact 46 and, thus, the anode 22 and, given the internal ground, the cathode contact 48 and, thus, the cathode 18. The controller 94, the processor 96, and the memory 98 would constitute a microcomputer and, given the internal clock or timer of the controller 94 as well as the ability to apply any potential or voltage between the anode 22 and the cathode 18 from the digital-to-analog converter 100, would be capable of performing a polarization or potentiostatic study as required according to the second and third preferred embodiments described above. Processing of the digital input data or signals by the processor 96 would involve appropriate analysis using developed algorithms which may include, but may not be limited to, either (a) pertinent factors and expressions involving oxygen tension, pH, the relationships among oxygen tension, pH, and equilibrium potentials of electrochemical reactions, and the rates of oxygen consumption and pH elevation as required by the first preferred embodiment described above; (b) graphic interpretations and linear, polynomial, and exponential regressions of either the cathodic potential curve or, if the anode 22 is indifferent, the interelectrode potential curve as required by the second preferred embodiment described above; or (c) mathematical calculations of the change in direct current with respect to the change in either cathodic potential or, if the anode 22 is indifferent, interelectrode potential as well as the change in direct current with respect to the square of the change in either cathodic potential or, if the anode 22 is indifferent, interelectrode potential as required by the third preferred embodiment described above. After the initial acquisition and analysis or processing of the analog input data or signals, faradic stimulation would be initiated through the application of a potential or voltage between the anode 22 and the cathode 18 from the digital-to-analog converter 100 where said potential or voltage would result in, depending upon the preferred embodiment, either a constant cathodic potential or, especially if the anode 22 is indifferent according to the second and third preferred embodiments, a constant interelectrode potential. On a periodic basis throughout the stimulation period, perhaps several times daily, the acquisition and analysis or processing of the analog input data or signals would be performed anew to permit adjustment of the faradic stimulus according to each of the preferred embodiments. Regardless of the preferred embodiment, the initial and periodic acquisition and analysis or processing of the analog input signals or data would be performed to initiate and adjust the faradic stimulus to account for initial differences between cases and temporal changes over the stimulation period exhibited by the electrochemical behavior of the cathode 18, the site of desired osteogenesis.

Although an automatic system is described above and illustrated in FIGS. 7A and 7B for a faradic device for stimulation of osteogenesis according to the principles of this present invention, a manual system with operator intervention may be adequate or suitable in certain cases or situations. Rather than the controller 94, processor 96, and the memory 98, an operator would command the initial and periodic acquisition of the analog input signals or data, process or analyze said data or signals using an appropriate peripheral device, as well as initiate and adjust the faradic stimulus through the digital to analog converter 100 or some other appropriate output component. Regardless of whether an automatic or a manual system is employed, said faradic device may be either totally implanted, external with each electrode physically connected to its contact, external with each electrode inductively coupled to its contact, or partially implanted and partially external if said device is separated into parts with communication between parts of said device established by digital transmitter and receiver. In addition, said faradic device may be modified or varied including, but not limited to, substitution or combination of major components and, for this reason, specifications with regard to any major component of said device are not provided here, especially when inevitable advancements in technology are considered. Finally, although a fracture of a long bone is illustrated in FIGS. 4A and 4B, this present invention is not limited to only fractures of only long bones but can be utilized to stimulate osteogenesis at any suitable tissue site in living tissue.

While this present invention has been described and illustrated in detail, it is to be clearly understood that the same is to be considered as illustrative and not restrictive in character, that only preferred embodiments have been shown and described, and that the spirit and scope of this present invention are to be limited only in accordance with the appended claims.

What is claimed is:

1. An apparatus for faradic stimulation of osteogenesis by control of electrochemical reactions occurring at a site of desired osteogenesis, said apparatus comprising:

means for producing faradic stimulation at said site;

closed-loop control means for maintaining said faradic stimulation at a level producing substantial osteogenic response while preventing initiation of hydrogen evolution, said closed-loop control means including means for repetitively identifying the onset of hydrogen evolution and adjusting said stimulation to a level near and below that corresponding to the identified onset of hydrogen evolution.

2. The apparatus of claim 1, wherein said closed-loop control means further includes means for measuring pH at said site.

3. The apparatus of claim 2, wherein said closed-loop control means further includes means for measuring oxygen tension at said site.

4. The apparatus of claim 1, wherein said closed-loop control means further includes means for measuring oxygen tension at said site.

5. The apparatus of claim 1, wherein said means for producing faradic stimulation includes a first electrode adapted to be placed at said site and a second electrode remote from said site, and wherein said closed-loop control means further includes means for measuring voltage and current between said first and second electrodes over a range sufficient to produce at least a portion of an identifiable voltage-current relationship having first, second and third regions, means for determining the transition zone between said second and third regions, and means for determining shifts in the transition zone.

6. The apparatus of claim 5, further comprising means for temporarily interrupting said faradic stimulation, and means for enabling said closed-loop control means during the period of interruption.

7. A method of faradic stimulation of osteogenesis by control of electrochemical reactions occurring at a site of desired osteogenesis, said method comprising the steps:

producing faradic stimulation at said site;

maintaining said faradic stimulation at a level producing substantial osteogenic response while preventing initiation of hydrogen evolution, said maintaining step including repetitively identifying the onset of hydrogen evolution and adjusting said stimulation to a level near and below that corresponding to the identified onset of hydrogen evolution.

8. The method of claim 7, further comprising the step of measuring pH at said site.

9. The method of claim 8, further comprising the step of measuring oxygen tension at said site.

10. The method of claim 7, further comprising the step of measuring oxygen tension at said site.

11. The method of claim 7, wherein said faradic stimulation is produced with a first electrode at said site and a second electrode remote from said site, and wherein said maintaining step further includes measuring voltage and current between said first and second electrodes over a range sufficient to produce at least a portion of an identifiable voltage-current relationship having first, second and third regions, determining the transition zone between said second and third regions, and determining shifts in the transition zone.

12. The method of claim 11, further comprising the steps of temporarily interrupting said faradic stimulation and performing said identifying and adjusting steps during the period of interruption.

13. A method for electrochemically controlled stimulation of osteogenesis, wherein said method comprises:

providing a first electrode with a conduction exposure;

providing a second electrode with a conductive exposure;

monitoring current and potential between said first electrode and said second electrode to ascertain the electrochemical behavior of said first electrode and said second electrode; and applying initially and adjusting periodically an electrical signal between said first electrode and said second electrode to cause and maintain an electrochemical process of a first type at said first electrode but not an electrochemical process of a second type at said first electrode.

14. A method according to claim 13, wherein said method further comprises:

providing a first reference electrode with a conductive exposure;

locating said first reference electrode remote from said first electrode and said second electrode; and monitoring potentials of said first electrode and said second electrode, each with respect to said first reference electrode, to further ascertain the electrochemical behavior of said first electrode and said second electrode.

15. A method according to claim 14, wherein said method further comprises:

providing a second reference electrode with conductive exposure;

providing a third reference electrode with a conductive exposure;

providing an oxygen tension electrode with an oxygen sensitive exposure;

providing a pH electrode with a hydrogen ion selective exposure;

locating said second reference electrode remote from said first electrode and said second electrode;

locating said third reference electrode remote from said first electrode and said second electrode;

locating said oxygen sensitive exposure of said oxygen tension electrode at said conductive exposure of said first electrode;

locating said hydrogen ion selective exposure of said pH electrode at said conductive exposure of said first electrode; and monitoring oxygen tension and pH at said conductive exposure of said first electrode to further ascertain the electrochemical behavior of said first electrode.

16. A method according to claim 15, wherein:

said second reference electrode is located in living tissue;

said third reference electrode is located in living tissue;

said oxygen tension electrode is located in living tissue; and said pH electrode is located in living tissue.

17. A method according to claim 14, wherein:

said first reference electrode is located in living tissue.

18. A method according to claim 13, wherein:

said first electrode is a negative electrode at which reduction occurs and from which current is being forced; and said second electrode is a positive electrode at which oxidation occurs and to which current is being forced.

19. A method according to claim 13, wherein:

said electrochemical process of said first type at said first electrode is beneficial to osteogenesis; and said electrochemical process of said second type at said first electrode is detrimental to osteogenesis.

20. A method according to claim 13, wherein:

said electrochemical process of said first type at said first electrode is consumption of oxygen and elevation of pH, with or without formation of hydrogen peroxide; and said electrochemical process of said second type at said first electrode is evolution of hydrogen and elevation of pH.

21. A method according to claim 13, wherein:

said first electrode is located with its conductive exposure at a tissue site in living tissue where osteogenesis is desired; and said second electrode is located with its conductive exposure in said living tissue remote from said tissue site.

22. A method according to claim 21, wherein:

said living tissue includes skin surface.

23. An apparatus for electrochemically controlled stimulation of osteogenesis, wherein said apparatus comprises:

a first electrode with a conductive exposure;

a second electrode with a conductive exposure;

an acquisition means for monitoring current and potential between said first electrode and said second electrode to ascertain the electrochemical behavior of said first electrode and said second electrode;

an electrical signal means for producing an electrical signal between said first electrode and said second electrode; and a control means for applying initially and adjusting periodically said electrical signal between said first electrode and said second electrode to cause and maintain an electrochemical process of a first type at said first electrode but not an electrochemical process of a second type at said first electrode.

24. An apparatus according to claim 23, wherein said apparatus further comprises:

a first reference electrode with a conductive exposure located remote from said first electrode and said second electrode; and an acquisition means for monitoring potentials of said first electrode and said second electrode, each with respect to said first reference electrode, to further ascertain the electrochemical behavior of said first electrode and said second electrode.

25. An apparatus according to claim 24, wherein said apparatus further comprises:

a second reference electrode with a conductive exposure located remote from said first electrode and said second electrode;

a third reference electrode with a conductive exposure located remote from said first electrode and said second electrode;

an oxygen tension electrode with an oxygen sensitive exposure located at said conductive exposure of said first electrode;

a pH electrode with an hydrogen ion selective exposure located at said conductive exposure of said first electrode; and an acquisition means for monitoring oxygen tension and pH at said conductive exposure of said first electrode to further ascertain the electrochemical behavior of said first electrode.

26. An apparatus according to claim 25, wherein:

said second reference electrode is adapted to be located in living tissue;

said third reference electrode is adapted to be located in living tissue;

said oxygen tension electrode is adapted to be located in living tissue; and said pH electrode is adapted to be located in living tissue.

27. An apparatus according to claim 24, wherein:

said first reference electrode is adapted to be located in living tissue.

28. An apparatus according to claim 23, wherein:

said first electrode is a negative electrode at which reduction occurs and from which current is being forced; and said second electrode is a positive electrode at which oxidation occurs and to which current is being forced.

29. An apparatus according to claim 23, wherein:

said electrochemical process of said first type at said first electrode is beneficial to osteogenesis; and said electrochemical process of said second type at said first electrode is detrimental to osteogenesis.

30. An apparatus according to claim 23, wherein:

said electrochemical process of said first type at said first electrode is consumption of oxygen and elevation of pH, with or without formation of hydrogen peroxide; and said electrochemical process of said first type at said first electrode is evolution of hydrogen and elevation of pH.

31. An apparatus according to claim 23, wherein:

said first electrode is adapted to be located with its conductive exposure at a tissue site in living tissue where osteogenesis is desired; and said second electrode is adapted to be located with its conductive exposure in said living tissue remote from said tissue site.

32. An apparatus according to claim 31, wherein:

said living tissue includes skin surface.

\* \* \* \* \*